(12) United States Patent
Shallcross

(10) Patent No.: US 7,611,626 B2
(45) Date of Patent: Nov. 3, 2009

(54) ROTATING MAGNETIC DEVICE UTILIZING SACRED GEOMETRY

(76) Inventor: Kim Shallcross, 8045 Appleby Line, Milton, Ontario (CA) L9T 2Y1

( * ) Notice: Subject to any disclaimer, the term of this patent is extended or adjusted under 35 U.S.C. 154(b) by 261 days.

(21) Appl. No.: 11/292,664

(22) Filed: Dec. 2, 2005

(65) Prior Publication Data

US 2006/0138891 A1 Jun. 29, 2006

(30) Foreign Application Priority Data

Dec. 2, 2004 (CA) .................................... 2488776

(51) Int. Cl.
*C02F 1/48* (2006.01)
(52) U.S. Cl. ................... 210/222; 210/223; 210/695
(58) Field of Classification Search ................. 210/222, 210/223, 695
See application file for complete search history.

(56) References Cited

U.S. PATENT DOCUMENTS 3,959,145 A * 5/1976 Lundquist et al. ........... 210/223

FOREIGN PATENT DOCUMENTS

WO WO 2004007377 A1 * 1/2004

* cited by examiner

*Primary Examiner*—David A Reifsnyder
(74) *Attorney, Agent, or Firm*—Polsinelli Shughart PC; Richard P. Stitt

(57) ABSTRACT

A device for healing or purification having magnets configured in a pattern conforming to sacred geometry, adapted for rotation about an axis. The device is useful for purifying water and breaking down toxic waste and environmental pollutants from automobiles and industry in water, food, soil and air.

13 Claims, 2 Drawing Sheets

ROTATING MAGNETIC DEVICE UTILIZING SACRED GEOMETRY

CROSS REFERENCE TO RELATED APPLICATION

This application claims priority to Canadian Patent Application No. 2,488,776 filed Dec. 2, 2004.

BACKGROUND OF THE INVENTION

The present invention relates to the field of purification and healing devices. In particular, the present invention provides an apparatus that utilizes the rotation of magnetic fields constructed in patterns dictated by sacred geometry.

There have been devices, including that shown in applicant's pending International Application No. PCT CA03/00966, that utilize the effect of rotating magnetic fields to purify water, food and the like, This device, while quite functional, is rather bulky, and uses a large electric motor to rotate a heavy circular array of magnets to achieve results.

Now, the actual mechanism by which purification of water, food and the like occurs in a rotating magnetic field is not precisely known. In "About strange effects related to rotating magnetic systems" by M. Pitkänen, University of Helsinki, the author suggest that gravitational anomalies may affect macroscopic objects in rotating magnetic systems. Moreover, negative energy spacetime sheets are generated by rotating magnetic fields, resulting in a quantum system in which particle energies are negative. However, as the author points out, this does not result in "sucking energy from the external world." Rather, negative energy is fed into the field.

The present inventor theorizes that it is the negative energy thus liberated that affects toxins, virus and bacteria particles, using aberrants commonly referred to as "superbugs."

SUMMARY OF THE INVENTION

The object of the present invention, therefore, is to provide an apparatus utilizing the inventor's previous developments in the field of rotating magnetic fields, to provide a more compact and efficient device for purification of food, water, air and soil, and direct application to human and animal body surfaces for healing. In order to achieve this object, the present invention utilizes the principles and patterns of sacred geometry.

By the term "sacred geometry," the applicant does not mean to imply that the present invention has religious significance. The term sacred geometry is a technical term of art used to refer to a number of basic geometrical patterns that have also been used by humanity over the millennia in religious rituals because of the patterns' fundamental connection with nature and humanity.

In a broad sense, sacred geometry can be said to be patterns and figures created using one of five basic geometrical ratios: Pi, $\sqrt{2}$, $\sqrt{5}$, $\sqrt{3}$, Phi.

Pi is the ratio of the diameter of a circle to its circumference.

$\sqrt{2}$ is the length of the diagonal of a square with sides of length 1.

$\sqrt{5}$ is the length of a diagonal of a rectangle with sides 1 and 2.

$\sqrt{3}$ is the length of a cord connecting the points of intersection of two circles of radius 1, when the circumference of each intersects the centre of the other.

Phi–1+$\sqrt{5}$/2 is a naturally occurring ratio prevalent in animal and plant skeletal structures; it is also referred to as the golden ratio. Most naturally occurring fractal patterns, such as snow flakes, tree shapes and so on, follow the golden ratio.

Sacred geometrical patterns, then, are patterns constructed using the sacred geometrical ratios, and are exemplified by the Seed of Life pattern, which will be used herein for example purposes. Other sacred geometrical shapes and patterns include, but are not limited to, pentagons, pentagrams, hexagrams, equilateral triangles, squares, rectangles with 2:1 ratio, vesica pisces, and three-dimensional structures including the pyramid and the Kathara grid. Other shapes and structures will be apparent to one versed in the field.

In a broad aspect, then, the present invention relates to a device for healing or purification having magnets configured in a pattern conforming to sacred geometry, adapted for rotation about an axis.

DESCRIPTION OF THE DRAWINGS

In drawings that illustrate the present invention by way of example.

DESCRIPTION OF THE PREFERRED EMBODIMENTS

Figure 1:
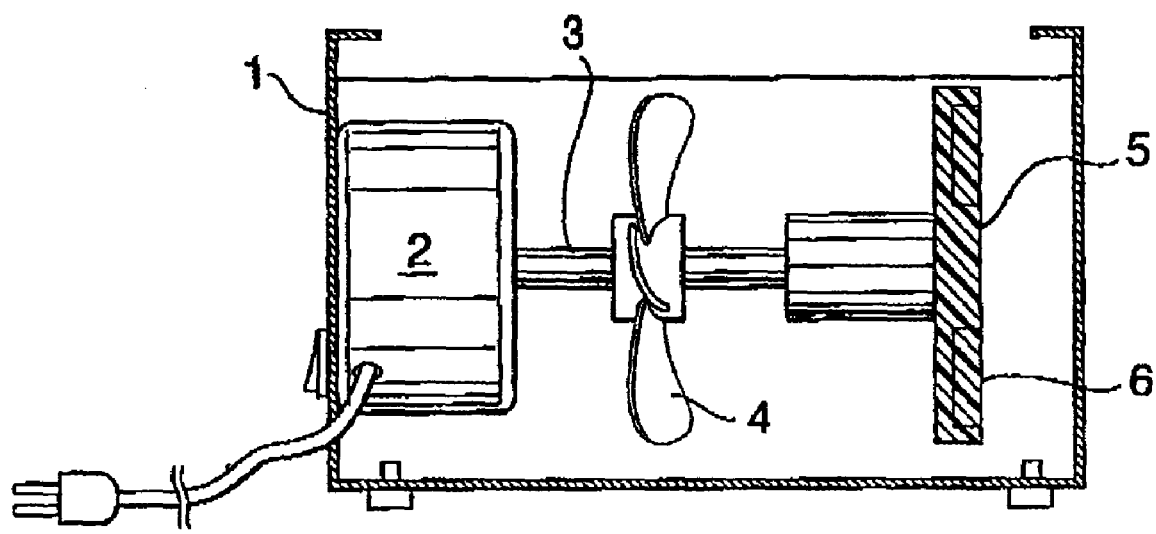
FIG. 1 is a schematic cross-sectional view of a device manufactured according to a first embodiment of the present invention, with its protective cover removed.

Referring now to the drawings, the present invention provides a device that may itself assume virtually any shape. Typically, it will be a compact box 1, with access to the interior thereof being possible by the removal of fasteners such as bolts or screws.

The box is made of metal or rigid plastic. Other materials, such as wood, fiberglass, ceramics or the like may also be used. A motor 2, such as an electric motor, is mounted in the box 1. Motor 2 is typically powered by connection to the electrical mains, but may alternatively be battery powered, solar powered, hand-cranked, or powered by any other known means. Motor 2 has a driven rotating shaft 3 extending therefrom, A cooling fan 4 may be mounted on the shaft, to keep the motor cool during long periods of operation, for instance if the device is being used to treat a water supply.

At the end of the shaft 3 is mounted a support plate 5, onto which magnets 6 are fastened. The plate may be made of any suitable substance, such as high density polyethylene. Magnets 6 are typically strong magnets such as iron boron neodymium magnets, available from a number of sources.

Figure 2:
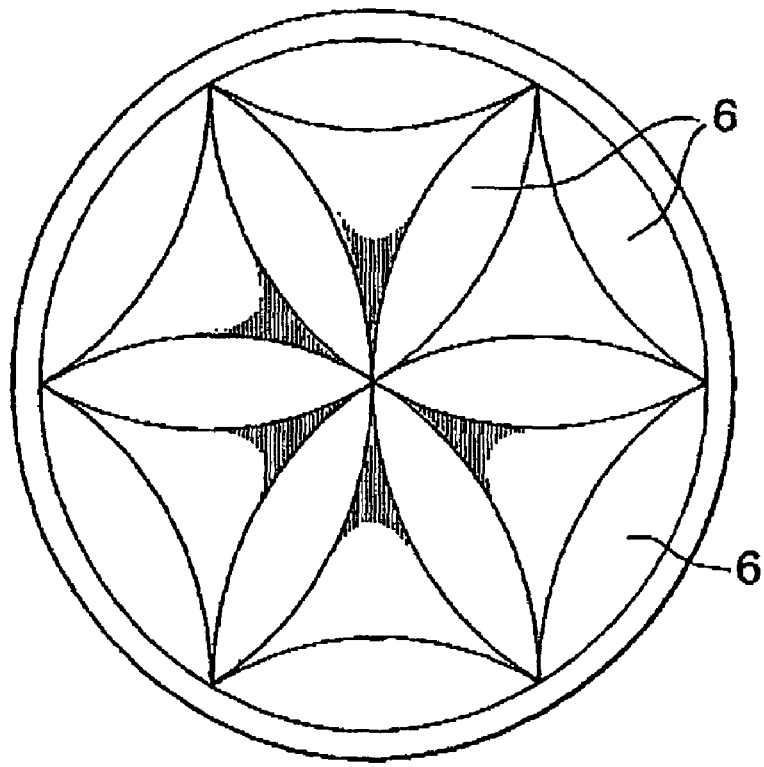
FIG. 2 is a schematic view of the layout of magnets on the rotating plate of the device of FIG. 1.

As can be seen from FIG. 2, the magnets 6 are laid out in a sacred geometrical pattern and affixed to support plate 5. Preferably, the pattern will be rotationally symmetrical about the centre of shaft 3, to permit the plate to rotate without wobbling.

The magnets 6 are cut, for instance by laser cutting, but by any suitable means, into the lens shape of the elements of the seed of life, in the embodiment illustrated. The magnets, it will be noted, may be electromagnets, or permanent magnets, since the field created will not differ substantially.

The device of the present invention has practical application as a means to purify water or food, to kill pathogens and break down toxins. The device is also useful for direct application to a human body to assist in restoring circulation, treating inflammation, ulceration, viral and bacterial infections, and as a general tonic.

As noted above, the magnets may be set out in other patterns for more specific use with other pathogens and toxins to obtain similar results. The seed of life pattern is a particularly advantageous pattern in that it allows one to concentrate the overlapping fields of a large number of magnets in a tight, rotationally symmetrical pattern Turning now to FIGS. 3 to 6, two advantageous embodiments of the present invention, using a three-dimensional array of magnets, are shown.

Figure 3:
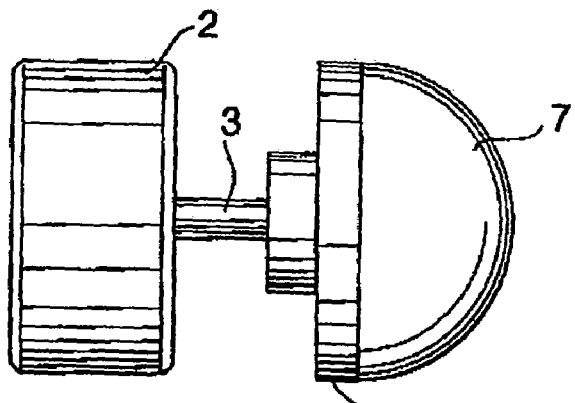
FIG. 3 is a schematic of an embodiment of the present invention using a hemispherical rotating magnet head.
Figure 4:
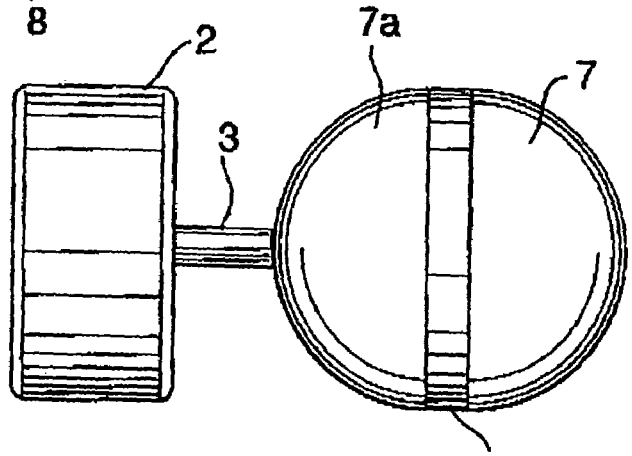
FIG. 4 is a schematic of an embodiment of the present invention using a symmetrically disposed pair of hemispherically shaped rotating magnet heads.

In the schematics of FIGS. 3 and 4, plate 5 having magnets mounted therein is replaced by a plate 8 mounted for rotation on shaft 3 that is driven by motor 2. In FIG. 3, a single hemispherical magnet head is mounted for rotation on plate 8. In FIG. 4, a pair of heads 7 and 7a are disposed symmetrically on shaft 3. It will be understood that in this embodiment, the innermost magnet head 7a will have a bore formed thereon to accommodate the shaft 3.

Figure 5:
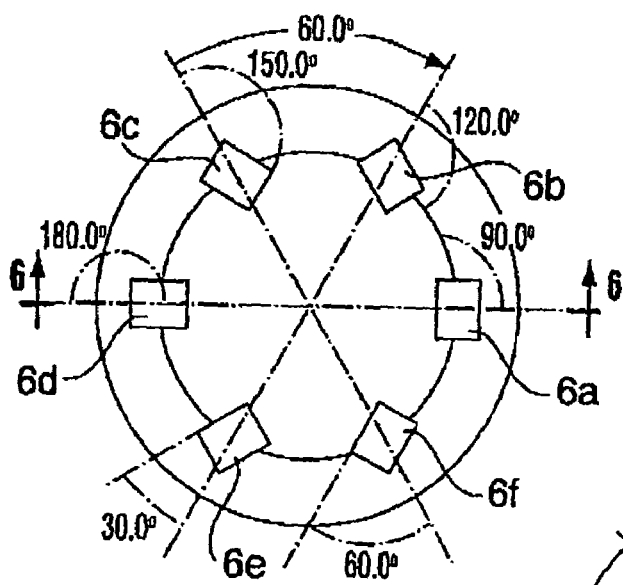
FIG. 5 is a schematic of the magnet layout of a hemispherical magnet head according to the present invention.
Figure 6:
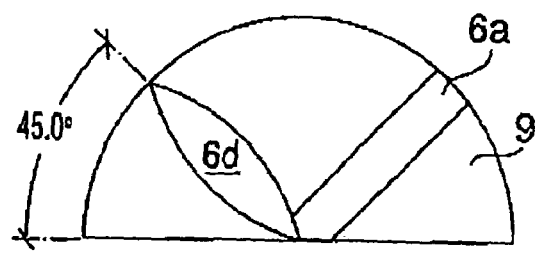
FIG. 6 is a cross-sectional view through line 6-6 of FIG. 5.

Turning to FIGS. 5 and 6, in FIG. 5, the layout of magnets in a hemispherical head 7 is shown. A series of six magnets 6, each one shaped like the magnets used in the flat assembly shown in FIG. 2, are mounted in a hemispherical matrix 9 of a non-magnetic plastic material such as polyethylene, polyurethane, or a similar rigid formable plastic material, The matrix is molded around the magnets, to fix them in place. Each of the six magnets, 6a, 6b, 6c, 6d, 6e and 6f is mounted in the matrix with one end near the radial centre of the hemisphere, and the other end near the outer periphery, as shown in FIG. 6. Each magnet is, however, rotated on its longitudinal axis by 30° relative to its clockwise neighbor, whereby diametrically opposed magnets 6a and 6d are rotated by 90° relative to each other. It has been found that this arrangement provides a vortex of interacting magnetic fields that will be concentrated along the axis of shaft 3, extending away from the rotating magnetic head.

It will be understood that other three-dimensional arrays of magnets will also be possible, as will be clear to one skilled in the art in light of the present disclosure.

Having thus described the invention, what is claimed as new and desired to be secured by Letters Patent, is as follows:

1. A device for healing or purification said device comprising:
   a shaft, said shaft connected to an electric motor for rotating said shaft,
   a fan mounted on said shaft for cooling said motor,
   a flat plate mounted on said shaft transverse to the rotational axis the said shaft, and
   a plurality of magnets affixed to said plate in a pattern rotationally symmetrical about the centre of the rotational axis of said shaft, said pattern being a seed of life pattern.

2. A device as claimed in claim 1, wherein said seed of life pattern is made up of six to twelve lens-shaped magnets arranged in a circular pattern, encompassing six to twelve similar lens-shaped magnets radiating from the centre of the circular pattern to the points of contact of the magnets in the circular pattern.

3. A device as claimed in claim 2, wherein said magnets are iron boron neodymium alloy permanent magnets.

4. A device as claimed in claim 2, wherein said magnets are electromagnets.

5. A device for healing or purification comprising a plurality of magnets at least some of which are arranged in a sacred geometrical seed of life pattern and which are mounted in a non-magnetic matrix or affixed to a non-magnetic plate.

6. A device as claimed in claim 5, including a three-dimensional array of magnets.

7. A device as claimed in claim 6 wherein said magnets are set in a hemispherical matrix of a plastic material.

8. A device as claimed in claim 7 wherein said array comprises from 6 to 12 lens-shaped magnets, each centered on the radial center of said hemispherical matrix and extending to the exterior perimeter thereof.

9. A device as claimed in claim 8 wherein each said magnet extends at 45 degrees from the base of said hemisphere.

10. A device as claimed in claim 9 wherein said magnets are spaced 60 degrees apart from one another.

11. A device as claimed in claim 10 wherein each magnet is rotated 30 degrees about its longitudinal axis relative to the clockwise next magnet.

12. A device as claimed in claim 11 further comprising first and second hemispherical matrices wherein an at least one of said hemispherical matrices having said plurality of magnets mounted in said hemispherical matrix comprises magnets in said seed of life pattern and said first and second hemispherical matrices are mounted having a flat face of said first hemispherical matrix is positioned opposite a flat fact of said second hemispherical matrix.

13. A device as claimed in claim 5, wherein said magnets are iron boron neodymium alloy permanent magnets.

* * * * *